United States Patent [19]

Gelbein

[11] 4,261,899
[45] Apr. 14, 1981

[54] PHTHALIC ANHYDRIDE REACTION SYSTEM

[75] Inventor: Abraham P. Gelbein, Morristown, N.J.

[73] Assignee: Chem Systems Inc., New York, N.Y.

[21] Appl. No.: 144,585

[22] Filed: Apr. 28, 1980

[51] Int. Cl.$^3$ .......................................... C07D 307/89
[52] U.S. Cl. ................................................ 260/346.4
[58] Field of Search ..................................... 260/346.4

[56] References Cited

U.S. PATENT DOCUMENTS

| | | | |
|---|---|---|---|
| 3,565,919 | 2/1971 | Friedrichsen et al. | 260/346.4 |
| 3,600,440 | 8/1971 | Foster et al. | 260/346.4 X |

*Primary Examiner*—Richard Raymond

*Attorney, Agent, or Firm*—Bert J. Lewen

[57] ABSTRACT

In a process for preparing phthalic anhydride, o-xylene is oxidized with air in a dilute phase transported bed reactor. The reaction is initiated with an o-xylene concentration above the upper flammability limit. Air is injected to a plurality of points along the reactor so as to prevent the oxygen concentration in the reactor from falling too low to maintain catalyst activity, while, at the same time, staying outside of the flammability envelope of the organic-oxygen mixtures. The process permits use of overall o-xylene/oxygen ratios which are substantially higher than were heretofore possible because of safety considerations, thereby minimizing the quantity of inert gases in the system, which reduces the size the complexity of the product recovery system.

7 Claims, 2 Drawing Figures

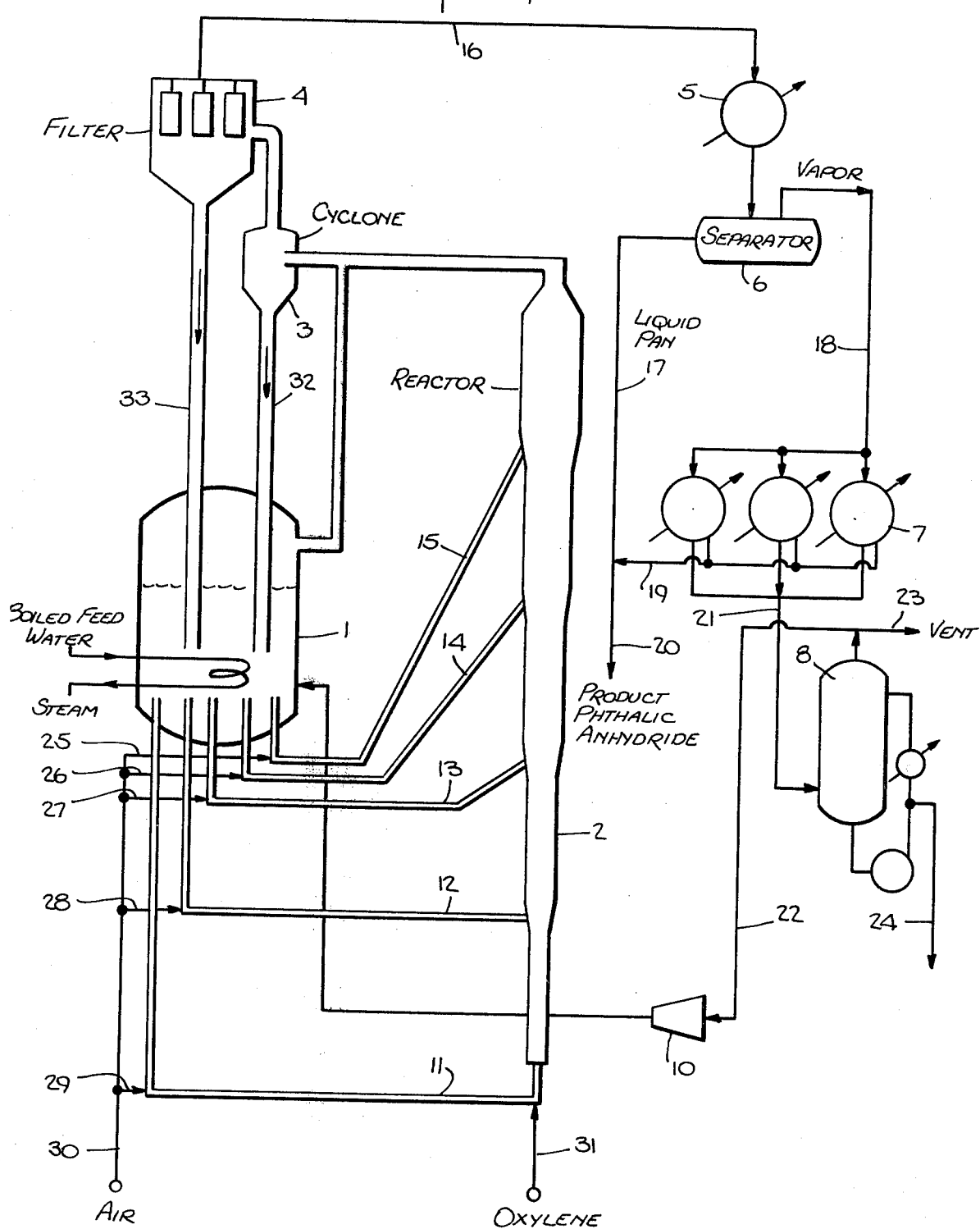

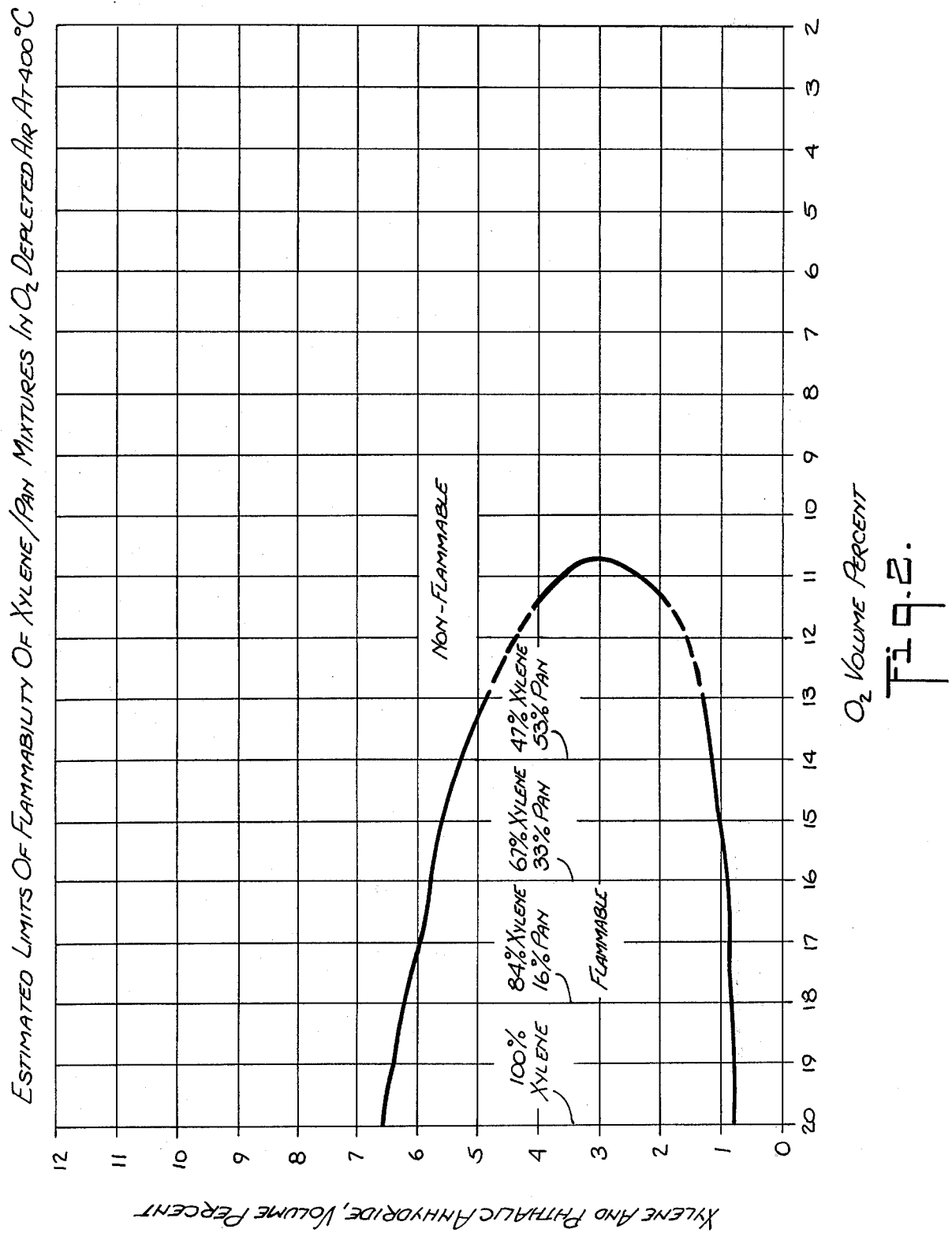

PHTHALIC ANHYDRIDE REACTION SYSTEM

BACKGROUND OF THE INVENTION

Phthalic anhydride is conventionally produced either by the oxidation of naphthalene with molecular oxygen over a fixed or fluid bed catalyst or by the oxidation of ortho-xylene with molecular oxygen over a fixed bed catalyst. These oxidation reactions are highly exothermic, and, therefore, it is desirable to conduct them in a fluidized bed reactor where high heat transfer rates may be achieved to obtain good temperature control. In a fixed bed system, temperature control is difficult and is achieved by using a multiplicity of small diameter tubes contained within a shell in which a coolant such as molten $NaNO_3/NaNO_2$ is circulated. The heat of reaction is removed from the coolant by circulation through an external heat exchanger. This system is complex and costly.

While it has been found, in the case of naphthalene oxidation, that equally satisfactory results can be achieved in either fixed or fluid beds, such is not the case of o-xylene oxidation. Attempts to conduct the o-xylene oxidation reaction in a fluid bed have been unsuccessful because a suitable fluidizable catalyst has not heretofore been readily available, and because the reaction is best carried out in a short residence time-plug flow regime, conditions which cannot be attained in a conventional fluid bed reactor.

Several moving bed type reactor systems have been described in the art for the purpose of retaining the good heat transfer characteristics of the fluid bed system, while at the same time attempting a plug flow regime.

U.S. Pat. No. 3,600,440 to Shell describes a compact moving bed system. In this system temperature control is good and backmixing of gases can be minimized, but movement of the solids is difficult and impractical. Further, while it is suggested that the explosion hazard which exists when operating in the flammability region can be eliminated because of the good heat transfer, this would be a very dangerous practice. This patent, while mentioning the oxidation of naphthalene, does not teach that the system is applicable to o-xylene oxidation.

U.S. Pat. No. 3,565,919 describes a fluidized bed catalyst for converting o-xylene to phthalic anhydride. Though a broad range of particle size is claimed, the exemplified particles have mean diameters in the range of 0.1 to 0.4 mm. Such process, wherein the catalyst particles as shown in the examples are fluidized vigorously in the presence of porcelain spheres, permits backmixing and would not achieve the desired plug flow.

U.S. Pat. No. 2,526,689 to Standard Oil describes a dense phase fluidized bed transport system which utilizes intermediate size particles (40 to 80 mesh). The operating regime in this system would result in significant backmixing of both catalyst particles and reacting gases. Furthermore, the catalysts described are not practical, i.e., they have poor physical strength and reported conversion of o-xylene to phthalic anhydride is impractically low.

A reactor system which retains the good heat transfer characteristics of the fluidized bed system and the plug flow characteristics of the fixed bed system is the dilute phase transport reactor system. In this system, particles size is small enough and gas velocity is high enough to ensure that particles and gases are in essentially plug flow motion in the reactor. Wainwright and Hoffman, in *Chemical Reaction Engineering II, Advances in Chemistry*, V. 133 (1974), pages (670-685, evaluated such a system for the oxidation of o-xylene to phthalic anhydride. The selectivity to phthalic anhydride was very poor, however.

Furthermore, the transported bed reactor taught is also unsatisfactory because complicated equipment is required, particularly in the product recovery system. This complication is largely because it was believed that, for safety considerations, the oxidation should be performed at oxygen concentrations below the flammability limit. Simply stated, in order to avoid the danger of explosion, it is generally understood that the reactor should not contain more than 1 mole % or organic constituents. Because of this required dilution, only very low concentrations of the reaction product appear in the reaction effluent and large quantities of inerts (primarily nitrogen) and unreacted effluent and large quantities of inerts (primarily nitrogen) and unreacted oxygen pass through the reactor and the recovery system. With the other alternative, that of operating with a feed composition above the upper flammability limit, i.e., 6 to 10 mole % organics, only about 50% conversion is achieved and a large amount of xylene has to be recovered and recycled. Still another factor is that during the course of the reaction the oxygen concentration must be maintained above approximately 5 mole % (i.e., a partial pressure of 0.05 atm.), because, at lower concentrations, catalyst activity is not maintained. The ideal objective of 100% conversion of o-xylene with the introduction of a minimum of inerts could only be obtained with air as the oxidant at approximately 3 mole % organics in the feed, a concentration directly in the middle of the flammable region!

Other references relating to the plug flow catalytic reaction include P. H. Calderbank et al., "The Prediction of the Performance of Packed-Bed Catalytic Reactors in the Air-Oxidation of o-Xylene," *Chemical Engineering Science*, 1977, Vol. 32, pp. 1435-1443, and M. S. Wainwright et al., "The Oxidation of Ortho-xylene on Vanadium Pentoxide Catalysts," *The Canadian Journal of Chemical Engineering*, vol. 55, October 1977, pp. 552-5634. To the extent operation in the explosive limit is taught in these references, the process is too dangerous to practice commercially. To the extent these references show the use of o-xylene concentrations of about 1 mole %, such process suffers from the drawback of requiring the costly equipment for the processing of large volumes of inert gas.

Gulf Research & Development Co., U.S. Pat. No. 4,102,914, shows a "fast fluidization" reactor for the ammoxidation of propylene with stagewise oxygen feed, but its teaching is solely restricted to preparing acrylonitrile.

BRIEF SUMMARY OF THE INVENTION

This invention relates to a process for preparing phthalic anhydride from ortho-xylene by oxidation in a dilute phase transported bed reactor. More specifically, this invention teaches a method for performing the reaction in a reactor where the oxygen-containing gas, preferably air, is supplied to the system at a plurality of spaced points along the reactor. By following this procedure, conversions approaching 100% may be achieved, while at the same time minimizing the amount of inert material passed through the system. The entire reaction is conducted outside of the explosive range.

BRIEF DESCRIPTION OF THE DRAWINGS

FIG. 1 describes schematically the dilute phase transported bed reactor of the invention and the ancillary equipment.

FIG. 2 shows graphically the estimated limits of flammability of a xylene and phthalic anhydride mixture in oxygen-depleted air at 400° C.

DETAILED DESCRIPTION OF THE DRAWINGS

In accordance with the invention, it has been discovered that the transported bed reactor system may be adapted to operate outside of the flammability region by introducing the oxygen necessary for the reaction at a plurality of spaced inlets along the reactor. In contrast, substantially all of the o-xylene is introduced at one end of the reactor. By so operating the transported bed reactor, an organic-rich feed may safely be used and the oxygen concentration maintained sufficiently high to fully activate the catalyst.

To more fully describe the invention, attention is directed to FIG. 1. Basically, the system consists of a dilute-phase transported bed reactor 2 and a catalyst fluidizing vessel 1. This embodiment of the invention shows the introduction of the air via line 30. Thereafter, the air enters a plurality of inlet lines 25, 26, 27, 28, and 29. The fluidized catalyst enters the reaction after admixture with the incoming air in inlet lines 11, 12, 13, 14 and 15. In this preferred mode of operation, the riser reactor is operated adiabatically using the sensible heat capacity of the solid catalyst particles to absorb the major portion of the heat of reaction. Accordingly, the temperature of the catalyst in the reactor increases as it passes from the inlet to the outlet. The reactor illustrated consists of five separate zones, each of which is provided with an inlet means for a portion of the air and catalyst. The first zone also receives all of the o-xylene charge. Where five zones are used, approximately 20% of the total air requirements are fed to each zone. The temperature of the catalyst entering the riser, the mixture, the residence time and the catalyst concentration, i.e., the weight of catalyst per unit volume of gas, are controlled so that the oxygen partial pressure at the outlet of each zone is about 0.05 atmosphere. This operation permits the reaction to proceed outside of the flammable region at all times.

In a preferred mode, the reactor riser illustrated in FIG. 1 is constructed so that the superficial velocity in each zone is about 12 meters/sec. (40 ft/sec). The superficial velocity is the volumetric flow rate of the gas plus the solids, divided by riser cross-sectional area. The mixture density (i.e., total weight of catalyst and gas divided by total volume of catalyst and gas) in each zone is 32 kg/m$^3$ (2 lbs/ft$^3$), the feed catalyst temperature approximately 400° C., and the total residence time in the riser approximately 2 secs. The following table shows approximate distribution of the residence time in each reaction zone:

| Zone Number | Distribution, % |
|---|---|
| 1 | 5 |
| 2 | 7 |
| 3 | 10 |
| 4 | 18 |
| 5 | 60 |

On the basis, the reactor riser illustrated in FIG. 1 is constructed as follows:

| Zone Number | Inside Diameter, cm. | Length, cm. |
|---|---|---|
| 1 | 48 | 150 |
| 2 | 65 | 215 |
| 3 | 77 | 305 |
| 4 | 90 | 550 |
| 5 | 100 | 1830 |

The foregoing dimensions are selected in conjunction with the consideration of the air and catalyst flow rates in lines 25–29 and the o-xylene feed rate in line 31. These are 282 kg-moles/hr, 182,000 kg/hr, and 45 kg-moles/hr, respectively. The catalyst is transported upwardly through the riser reactor 2 by the reacting gases and thereafter exits the top of the reactor along with the reactor effluent and enters the cyclone 3. The separated catalyst is returned to the catalyst vessel 1 via line 32 while the effluent gases, containing a small amount of catalyst, pass to filter 4 for the final separation of the catalyst from the product gases. The catalyst collected in the filter 4 is also returned to the catalyst vessel 1 through line 33. The gaseous reactor effluent, now free of catalyst, leaves the filter 4 via line 16 and is cooled in two stages in heat exchanger 5 to recover the sensible heat of the gases and condense a portion of the phthalic anhydride as a liquid. The cooled stream passes to the separator 6 wherein liquid phthalic anhydride is removed from the system via line 17. The non-condensed vapor leaves the separator 6 via line 18, containing residual phthalic anhydride, intermediate oxidation products, carbon oxides, water, oxygen and nitrogen, and is further cooled in the swing condenser 7 to separate the remaining phthalic anhydride. The condenser "swings" through a cooling and heating cycle first to condense the phthalic anhydride as a solid and then to melt it for recovery as a liquid. The liquid phthalic anhydride is removed from the swing condenser via line 19 and the total phthalic anhydride sent to purification (not shown) via line 20. The effluent gases from the swing condenser 7 are passed via line 21 to the tower 8 where they are scrubbed and cooled to recover organic condensables and the water of reaction. These are removed from the system via line 24 for further processing. The effluent gas from the tower 8 is split into a vent stream 23 and a recycle stream 22. The vent stream contains the carbon oxides produced in the reaction, unreacted oxygen, and nitrogen. The recycle stream, after compression in compressor 10, is sent to the catalyst vessel 1 to fluidize the catalyst.

A catalyst useful for this invention must have good selectivity and activity for the air oxidation of o-xylene to phthalic anhydride, high attrition resistance, spherical shape, and an average particle size of less than 100 microns. The catalyst used in this example is a TiO$_2$/V$_2$O$_5$ catalyst supported on silica gel having a particle size of 60 micron, prepared as described in Example 2 of U.S. Pat. No. 3,565,919. This catalyst contains about 23% TiO$_2$, 9% V$_2$O$_5$ and 68% silica gel.

Table 1 sets forth, on a molar basis, the compositions in the various zones of the reactor, as well as the molar percentage of the oxygen and xylene and phthalic anhydride entering and leaving each zone.

TABLE 1
COMPOSITION PROFILE FOR INCREMENTAL AIR ADDITION

| Component, Moles | Reaction Zone 1 In | 1 Out | 2 In | 2 Out | 3 In | 3 Out | 4 In | 4 Out | 5 In | 5 Out |
|---|---|---|---|---|---|---|---|---|---|---|
| Xylene | 100 | 80.85 | 80.85 | 60.68 | 60.68 | 40.51 | 40.51 | 20.34 | 20.34 | 0 |
| Phthalic Anhydride | — | 14.37 | 14.37 | 29.50 | 29.50 | 44.63 | 44.63 | 59.76 | 59.76 | 75.0 |
| $O_2$ | 129.8 | 36.41 | 166.19 | 67.84 | 197.62 | 99.28 | 229.06 | 130.72 | 260.5 | 161.4 |
| $N_2$ | 491.2 | 491.2 | 982.36 | 982.36 | 1473.54 | 1473.54 | 1964.72 | 1964.71 | 2455.9 | 2455.9 |
| $H_2O$ | — | 67.04 | 67.04 | 137.65 | 137.65 | 208.0 | 208.0 | 278.6 | 278.6 | 350.0 |
| $CO_2$ | — | 38.31 | 38.31 | 78.65 | 78.65 | 119.0 | 119.0 | 159.4 | 159.4 | 200.0 |
| Total | 721.0 | 728.2 | 1349.0 | 1356.8 | 1977.7 | 1984.9 | 2605.9 | 2613.5 | 3234.5 | 3242.3 |
| $O_2$, Mole % | 18.0 | 5.0 | 12.3 | 5.0 | 10.0 | 5.0 | 8.8 | 5.0 | 8.1 | 5.0 |
| Xylene & Phthalic Anhydride, Mole % | 13.9 | 13.1 | 7.61 | 6.6 | 4.6 | 4.3 | 3.3 | 3.1 | 2.5 | 2.3 |

As will be observed by considering Table 1 in conjunction with FIG. 2, the organic-to-oxygen concentration is such that at no time during the course of the reaction does it fall within the flammability limit. This can be readily observed by plotting mole percent oxygen and mole percent organics on FIG. 1.

Based on the above procedure and assuming essentially 100% conversion of o-xylene and the further constraint that the oxygen concentration in the reactor effluent always remains above 5 mole %, the following product feed and product compositions are obtained:

|  | Moles Feed | Product |
|---|---|---|
| o-Xylene | 100 | 0 |
| Phthalic Anhydride |  | 75 |
| $O_2$ | 648.9 | 161.4 |
| $N_2$ | 2455.9 | 2455.9 |
| $H_2O$ |  | 350 |
| $CO_2$ |  | 200 |
| TOTAL | 3204.8 | 3242.3 |

The total volume passing through the system is less than one-third of that required using the prior art procedure wherein the o-xylene and all of the air are added initially to the reactor and the reaction is carried out below the lower flammability limit.

The above example shows a preferred embodiment of the invention. It will be understood that many variations of the above teaching may be made without departing from the spirit of the invention.

For example, the temperature may vary from 300° to 500° C. Using a catalyst of the vanadium pentoxide-titanium dioxide type, the preferred temperature is generally about 400° C., though this may vary to some degree depending on the specific catalyst formulation. Naturally, the temperature may vary through the reaction bed because of the exothermic nature of the reaction. Generally the temperature differential should be in the range of not more than 30° C. With respect to the overall pressure in the reactor, generally this should be from 1 to 5 atmospheres. Two atmospheres is preferred, since this is sufficient to drive the gases through the reactor bed and the recovery system.

The oxygen containing gas used in the process is most preferably air, but the process may be applied to oxygen-enriched or depleted air or high purity oxygen. The portion of the oxygen added to each stage of the process is selected to insure that the organic concentration, i.e., the o-xylene plus the phthalic anhydride, is above or otherwise outside of the flammability limit. For example, with reference to Table 1 and FIG. 2, it will be noted that if a greater proportion of air is added to the first and second reactors the oxygen concentration might well fall into the explosive region. In the first stage, the inlet oxygen concentration will be highest, namely, about 15 to 20 mole %. In subsequent stages the amount at the inlet progressively decreases, until in the final stage it may be only 1 to 5 mole % above the outlet concentration.

The partial pressure of oxygen at the outlet of each zone should be about 0.05 atmosphere. This figure is equivalent to 5 mole % at atmospheric pressure. This limit is determined by the amount of oxygen necessary to maintain the activity of the particular catalyst and variations thereof may be readily determined by those skilled in the art.

While any catalyst which serves to convert o-xylene to phthalic anhydride may be adapted to the instant invention so long as it is sufficiently active and durable, most preferably supported catalysts impregnated with vanadium pentoxide and titanium dioxide in the anatase form are used. Of most importance is the particle size of the catalyst. Broadly, this may vary within the range of from about 40 to 100 microns, an approximately 60 micron particle size being most advantageous. Such catalysts are described in U.S. Pat. No. 3,565,919 and U.S. Pat. No. 3,926,846. Those preferred herein are supported on a support having a pore volume of from 0.15 to 1.0 cc/gm, e.g., alumina and silica-alumina, and an Attrition Index of less than 20. The latter is measured by subjecting a sample of the support to the high velocity jet of air (approximately 75,000 cm/sec) for one hour. The Attrition Index is defined as follows:

$$\text{Attrition Index} = (W_f - W_i)/W_I \times 100,$$

wherein $W_I$ is the weight initially of particles over 38 microns, $W_f$ is the weight of particles less than 38 microns after the attrition test, and $W_i$ is the weight of particles less than 38 microns initially.

The superficial velocity may be broadly from 6 to 15 meters per second and the mixture density in each zone from 2 to 65 kg/m³, preferably at least 15 kg/m³. It is these superficial mixture velocities and catalyst densities which are required to maintain the dilute phase transport reaction.

The total contact time of the o-xylene in the riser reactor is generally from 0.1 to 30 seconds, preferably from 0.5 to 10 seconds, and most desirably from 0.5 to 3 seconds.

I claim:

1. A process for the preparation of phthalic anhydride by the oxidation of ortho-xylene which comprises: introducing, into a first reaction zone, phthalic anhydride catalyst particles having a particle size of from 40 to 100 microns, o-xylene and a portion of the oxygen-containing gas required for the overall reaction, the proportion of the gaseous components being selected so that the partial pressure of oxygen is above 0.05 atmospheres and the o-xylene concentration is above the flammability region; maintaining the superficial velocity in said first reaction zone and the catalyst density so that the catalyst is transported through said first reaction zone in a dilute phase with plug flow; continuing the oxidation in said first reaction zone until the oxygen partial pressure is approximately 0.05 atmosphere; passing the effluent from said first reaction zone to a second reaction zone wherein additional oxygen-containing gas is added; conducting the oxidation in said second reaction zone until the oxygen partial pressure in said reaction zone is approximately 0.05 atmosphere; repeating the oxidation in subsequent reaction zones until substantially all of the o-xylene is oxidized; removing the effluent which contains gaseous products and phthalic anhydride catalyst from the last reaction zone of the reactor; separating the catalyst from the gaseous products and thereafter recycling said catalyst to the reactor; and separating the phthalic anhydride from the gaseous effluent as product.

2. The process of claim 1 wherein the reactor contains five reaction zones, and approximately 20% of the required oxygen is added to each reaction zone.

3. The process of claim 1 wheren the phthalic anhydride catalyst is supported vanadium pentoxide-titanium dioxide.

4. The process of claim 1 wherein the superficial velocity in each zone is between 6 and 15 meters per second and the density of the mixture is between 2 and 65 kilograms per cubic meter.

5. The process of claim 1 wherein the superficial velocity in each reaction zone is substantially the same.

6. A process for the preparation of phthalic anhydride by the air oxidation of ortho-xylene which comprises: introducing, into a first reaction zone, phthalic anhydride catalyst particles having a particle size of from 40 to 100 microns, o-xylene and a portion of the air required for the overall reaction, the proportion of the gaseous components being selected so that the partial pressure of oxygen is above 0.05 atmosphere and the o-xylene concentration is above the flammability region; maintaining the superficial velocity in said first reaction zone between 6 and 15 meters per second and the mixture density between 2 and 65 kilograms per cubic meter so that the catalyst bed is transported through said first reaction zone in a dilute phase with plug flow; oxidizing a portion of the xylene in the first reaction zone at a temperature from 300° to 500° C. and a pressure of from 1 to 5 atmospheres until the oxygen partial pressure is approximately 0.05 atmosphere; passing the effluent from said first reaction zone to a second reaction zone wherein additional air is added; maintaining dilute phase transported bed and continuing the oxidation in said second reaction zone within the same range of conditions described for said first reaction zone until the oxygen partial pressure in said reaction zone is approximately 0.05 atmosphere; repeating the oxidation in subsequent reaction zones until at least 98 mole % of the o-xylene is oxidized; removing the effluent which contains gaseous products and phthalic anhydride catalyst from the last reaction zone of the reactor; separating the catalyst from the gaseous products and thereafter recycling said catalyst to the reactor; and separating the phthalic anhydride from the gaseous effluent as product.

7. The process of claim 6 wherein the phthalic anhydride catalyst is a vanadium pentoxide-titanium dioxide catalyst supported on a catalyst support having a pore volume of from 0.15 to 1 cm$^3$/gm and an Attrition Index of less than 20.

* * * * *